(12) United States Patent
Fukushima et al.

(10) Patent No.: US 7,507,863 B2
(45) Date of Patent: Mar. 24, 2009

(54) PROCESS FOR PRODUCING NITROGEN-CONTAINING COMPOUNDS

(75) Inventors: Tetsuaki Fukushima, Wakayama (JP); Masaharu Jono, Wakayama (JP); Michio Terasaka, Wakayama (JP)

(73) Assignee: Kao Corporation, Tokyo (JP)

( * ) Notice: Subject to any disclaimer, the term of this patent is extended or adjusted under 35 U.S.C. 154(b) by 100 days.

(21) Appl. No.: 11/614,428

(22) Filed: Dec. 21, 2006

(65) Prior Publication Data

US 2007/0149818 A1 Jun. 28, 2007

(30) Foreign Application Priority Data

Dec. 28, 2005 (JP) ............................. 2005-379635

(51) Int. Cl.
*C07C 209/16* (2006.01)
*B01J 21/00* (2006.01)

(52) U.S. Cl. ....................................... 564/479; 502/113

(58) Field of Classification Search ....................... None
See application file for complete search history.

(56) References Cited

U.S. PATENT DOCUMENTS 7,183,438 B2 * 2/2007 Gerlach et al. ............... 564/397

FOREIGN PATENT DOCUMENTS

JP 8-176074 7/1996

OTHER PUBLICATIONS

Database CAPLUS on STN, Acc. No. 2003:737709, Gerlach et al., WO 2003/076386 A2 (Sep. 18, 2003) (abstract).*

* cited by examiner

*Primary Examiner*—Brian J Davis
(74) *Attorney, Agent, or Firm*—Oblon, Spivak, McClelland, Maier & Neustadt, P.C.

(57) ABSTRACT

The present invention relates to a process for producing an aliphatic amine, including the step of contacting a linear or branched, or cyclic aliphatic alcohol with ammonia and hydrogen in the presence of a catalyst containing (A) nickel, copper and zirconium components, and (B) at least one metal component selected from the group consisting of elements belonging to Group 1 of the Periodic Table. According to the process of the present invention, an aliphatic primary amine can be produced from the aliphatic alcohol with a good yield and a high productivity.

18 Claims, No Drawings

PROCESS FOR PRODUCING NITROGEN-CONTAINING COMPOUNDS

FIELD OF THE INVENTION

The present invention relates to a process for producing nitrogen-containing compounds, in particular, aliphatic amines.

BACKGROUND OF THE INVENTION

Aliphatic primary amines are important compounds in domestic and industrial application fields and have been used as raw materials for production of surfactants, fiber-treating agents, etc.

The aliphatic primary amines have been produced by various processes. As one of the production processes, there is known the method of contacting an aliphatic alcohol with ammonia and hydrogen in the presence of a catalyst. In the catalytic reaction, there has been used a nickel/copper-based catalyst or a noble metal-based catalyst.

As the process for producing amines from aliphatic alcohols using the nickel/copper-based catalyst, there is disclosed, for example, the process for producing amines from a primary or secondary alcohol and ammonia or a primary or secondary amine using hydrogen in the presence of a zirconium/copper/nickel catalyst in which a composition containing an oxygen-containing zirconium compound in an amount of 20 to 85% by weight in terms of $ZrO_2$, an oxygen-containing copper compound in an amount of 1 to 30% by weight in terms of CuO, an oxygen-containing nickel compound in an amount of 30 to 70% by weight in terms of NiO, an oxygen-containing molybdenum compound in an amount of 0.1 to 5% by weight in terms of $MoO_3$, and an oxygen-containing aluminum and/or manganese compound in an amount of 0 to 10% by weight in terms of $Al_2O_3$ or $MnO_2$ is used as a catalytically active material (refer to JP 8-176074A). Also, there is disclosed the process for producing amines from a primary or secondary alcohol and a nitrogen compound selected from the group consisting of ammonia and a primary or secondary amine at a temperature of 80 to 250° C. under a pressure of 0.1 to 40 MPa using hydrogen in the presence of a catalyst containing zirconium, copper and nickel but no oxygen-containing cobalt or molybdenum compound (refer to JP 11-180967A).

However, in these conventional techniques, the reactivity tends to be insufficient and the selectivity tends to be low.

SUMMARY OF THE INVENTION

The present invention relates to a process for producing an aliphatic amine, including the step of contacting a linear or branched, or cyclic aliphatic alcohol with ammonia and hydrogen in the presence of a catalyst containing (A) nickel, copper and zirconium components, and (B) at least one metal component selected from the group consisting of elements belonging to Group 1 of the Periodic Table.

DETAILED DESCRIPTION OF THE INVENTION

The present invention relates to a process for producing an aliphatic amine, in particular, an aliphatic primary amine, from an aliphatic alcohol with a good yield and a high productivity.

In the process for producing an aliphatic amine according to the present invention, as a raw material, there is used the linear or branched, or cyclic, saturated or unsaturated aliphatic alcohol. The aliphatic alcohol used as the raw material may be in the form of either an aliphatic primary alcohol or an aliphatic secondary alcohol.

Examples of the alcohol usable in the present invention include primary or secondary alcohols such as methyl alcohol, ethyl alcohol, n-propyl alcohol, isopropyl alcohol, n-butyl alcohol, isobutyl alcohol, n-pentyl alcohol, n-hexyl alcohol, tridecanol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, 3,7-dimethyloctyl alcohol, 2-propylheptyl alcohol, geraniol, dodecyl alcohols such as lauryl alcohol, tetradecyl alcohols such as myristyl alcohol, hexadecyl alcohols such as palmityl alcohol, octadecyl alcohols such as stearyl alcohol and oleyl alcohol, behenyl alcohol, and icosyl alcohols; cyclic alcohols such as cyclopentanol, cyclohexanol, cyclopentyl methanol, cyclopentenyl methanol, cyclohexyl methanol and cyclohexenyl methanol; amine alcohols such as ethanol amine, n-propanol amine, isopropanol amine, n-pentanol amine, n-hexanol amine, diethanol amine, N-alkyldiethylethanol amine, diisopropanol amine, N,N-dimethylaminoethanol, N,N-diethylaminoethanol, N,N-di-n-propylaminoethanol, N,N-diisopropylaminoethanol, N,N-di-n-butylaminoethanol, N,N-diisobutylaminoethanol, N,N-di-s-butylaminoethanol, N,N-di-t-butylaminoethanol, N,N-dimethylaminopropanol, N,N-diethylaminopropanol, N,N-di-n-propylaminopropanol, N,N-diisopropylaminopropanol, N,N-di-n-butylaminopropanol, N,N-diisobutylaminopropanol, N,N-di-s-butylaminopropanol, N,N-di-t-butylaminopropanol, 1-dimethylamino-4-pentanol and 1-diethylamino-4-pentanol; polyhydric alcohols such as ethylene glycol, 1,2-propylene glycol, 1,3-propylene glycol, diglycol, 1,4-butanediol, 1,5-pentanediol, 1,6-hexanediol and 2,2-bis[4-hydroxycyclohexyl]propane; alkoxy alcohols such as methoxy ethanol, propoxy ethanol and butoxy ethanol; and polyalcohols such as polyisobutyl alcohol and polypropyl alcohol.

In the present invention, among the above aliphatic alcohols, preferred are those aliphatic alcohols containing a linear or branched, or cyclic alkyl, alkenyl or alkynyl group having 1 to 22 carbon atoms, more preferred are those aliphatic alcohols containing a linear or branched, or cyclic alkyl, alkenyl or alkynyl group having 6 to 22 carbon atoms, and even more preferred are those linear aliphatic alcohols containing an alkyl, alkenyl or alkynyl group having 8 to 22 carbon atoms.

In the process for producing an aliphatic amine according to the present invention, there is used the catalyst containing (A) nickel, copper and zirconium components, and (B) at least one metal component selected from the group consisting of elements belonging to Group 1 of the Periodic Table (hereinafter occasionally referred to merely as a "nickel/copper-based catalyst").

In view of a sufficient catalytic activity as well as good selectivity and low costs, the nickel/copper-based catalyst used in the present invention contains as the component (A), the nickel component in an amount of preferably 10 to 55% by mass, more preferably 15 to 55% by mass and even more preferably 23 to 47% by mass in terms of metallic nickel on the basis of a total amount of the catalyst; the copper component in an amount of preferably 0.5 to 32% by mass, more preferably 2 to 28% by mass and even more preferably 4 to 24% by mass in terms of metallic copper on the basis of a total amount of the catalyst; and the zirconium component in an amount of preferably 10 to 63% by mass, more preferably 11 to 52% by mass and even more preferably 14 to 44% by mass in terms of metallic zirconium on the basis of a total amount of the catalyst.

Also, examples of the (B) at least one metal component selected from the group consisting of elements belonging to Group 1 of the Periodic Table include lithium, sodium, potassium, rubidium, cesium and francium. Among these metal elements, in view of a good catalytic activity, preferred are lithium, potassium and sodium, and more preferred is potassium. These metal components may be used alone or in combination of any two or more thereof.

In view of a sufficient catalytic activity as well as low costs, the nickel/copper-based catalyst contains the (B) at least one metal component selected from the group consisting of elements belonging to Group 1 of the Periodic Table in an amount of preferably 0.02 to 10% by mass, more preferably 0.03 to 2% by mass and even more preferably 0.05 to 1% by mass in terms of the metal element on the basis of a total amount of the catalyst.

The nickel/copper-based catalyst used in the present invention may be produced by using a nickel compound, a copper compound and a zirconium compound. Examples of the nickel compound, the copper compound and the zirconium compound include sulfates, nitrates, chlorides, etc., of nickel or copper, and nitrates, sulfates, oxynitrates, oxysulfates, oxychlorides, acetates, etc., of zirconium.

Upon producing the nickel/copper-based catalyst used in the present invention, an alkali is added to an aqueous solution containing the above nickel compound, copper compound and zirconium compound to adjust a pH of the solution to about 6 to 10 and preferably about 6 to 8, and then the obtained solution is aged to precipitate a mixture of the respective metal components. The alkali is not particularly limited, and examples of the alkali usable include sodium carbonate, sodium hydroxide, potassium carbonate and potassium hydroxide.

Thereafter, the resultant suspension is subjected to solid/liquid separation by filtration, etc. The thus obtained precipitate was fully washed with water, if required, and then intimately mixed with an aqueous solution containing a compound of an element belonging to Group 1 of the Periodic Table under stirring. The resultant mixture is subjected to heating and drying treatments, and then baked, thereby obtaining the aimed nickel/copper-based catalyst.

In the present invention, the above water-washing procedure is preferably conducted to such an extent that the obtained filtrate has an electric conductivity of 200 μS/cm or less, in order to prevent counter ions from remaining in the resultant catalyst. The mixing of the precipitate containing the respective nickel, copper and zirconium components with the aqueous solution containing the compound of the element belonging to Group 1 of the Periodic Table is usually conducted at a temperature of 20 to 95° C. and preferably 30 to 80° C.

The above drying treatment is preferably conducted at a temperature of 140° C. or lower under normal or reduced pressure. In addition, the baking is conducted at a temperature of preferably 300 to 800° C. and more preferably 400 to 600° C. for a period of usually 1 to 4 h, if required, while flowing air, nitrogen, etc., through the system.

Examples of the compound of the element belonging to Group 1 of the Periodic Table include nitrates, sulfates, chlorides, etc., of the element belonging to Group 1 of the Periodic Table. Among these compounds, preferred are nitrates of the element belonging to Group 1 of the Periodic Table. The compound of the element belonging to Group 1 of the Periodic Table may be added to the above water-washed precipitate containing the respective nickel, copper and zirconium components. Alternatively, the compound may be added simultaneously upon mixing the above nickel, copper and zirconium compounds with each other, or may be added to or mixed with a dried product of the precipitate containing the above nickel, copper and zirconium components.

The thus produced nickel/copper-based catalyst may be directly used, but is preferably previously subjected to reducing treatment when used as a catalyst for producing an aliphatic amine from a raw aliphatic alcohol. The reducing treatment may be performed, for example, by a vapor-phase reducing method in which the nickel/copper-based catalyst is reduced at a temperature of 100 to 300° C. and preferably 120 to 280° C. in a hydrogen atmosphere, or the method in which the nickel/copper-based catalyst is reduced in the raw alcohol at a temperature of 120 to 280° C. under a pressure of from normal pressure to 50 MPaG in a hydrogen atmosphere or under a hydrogen flow.

In the process for producing an aliphatic amine according to the present invention, the aliphatic alcohol as the raw material is contacted with ammonia and hydrogen in the presence of the thus produced nickel/copper-based catalyst to produce the aliphatic amine as the aimed product.

The catalytic reaction may be carried out in either a batch type closed system or a batch type flow system, or in a fixed bed flow system. The amount of the catalyst used varies depending upon the kind of reaction system used. In a batch type reaction system, in view of attaining good reactivity and selectivity, the catalyst is used in an amount of preferably 0.1 to 20% by mass and more preferably 0.5 to 10% by mass on the basis of the raw aliphatic alcohol. Also, in view of a good conversion of the raw alcohol, a good selectivity to primary amines and prevention of deactivation of the catalyst, the reaction temperature is from 120 to 280° C. and preferably from 180 to 250° C., and the reaction pressure is from normal pressure to 50 MPaG and preferably from 0.5 to 30 MPaG.

The molar ratio of ammonia to the aliphatic alcohol as the raw materials (ammonia/aliphatic alcohol) is usually from 0.5 to 10 and preferably from 2 to 7. Ammonia may be added separately from hydrogen, or may be introduced in the form of a mixed gas of ammonia and hydrogen.

The molar ratio of hydrogen to the aliphatic alcohol as initial charges (hydrogen/aliphatic alcohol) is preferably from 0.01 to 3.0 and more preferably from 0.02 to 2.0 when used in a batch type closed system. When used in a batch type flow system or a fixed bed flow system, the molar ratio of hydrogen initially flowing through the system to the aliphatic alcohol is preferably from 0.01 to 1.0 and more preferably from 0.02 to 0.8. However, in any of the above reaction methods, the molar ratios in the course of the respective reactions are not necessarily limited to the above-specified ranges.

According to the production process of the present invention, an aliphatic amine, in particular, an aliphatic primary amine, can be produced from an aliphatic alcohol with a good yield and a high productivity.

Thus, the process for producing an aliphatic amine according to the present invention provides such a method of producing an aliphatic amine, in particular, an aliphatic primary amine, from an aliphatic alcohol with a good yield and a high productivity. The thus obtained aliphatic amine is an important compound in domestic or industrial application fields, and can be suitably used as raw materials for production of surfactants, fiber-treating agents, etc.

The present invention is described in more detail by referring to the following examples. However, it should be noted that these examples are only illustrative and not intended to limit the invention thereto.

PREPARATION EXAMPLE 1

To 900 g of ion-exchange water were added 39.5 g of nickel nitrate hexahydrate, 4.9 g of copper nitrate hexahydrate and 40.1 g of an aqueous solution containing zirconium acetate in an amount of 15% by mass in terms of Zr, and the resultant mixture was heated to 70° C. under stirring. An aqueous solution containing 20% by mass of sodium carbonate was dropped into the mixture for about 1 h until a pH of the solution reached 7.0. Thereafter, while maintaining a pH of the solution at 7.0, the solution was aged at 70° C. for about 2h. The resultant suspension was cooled to about 40° C., filtered and then washed with ion-exchange water until an electric conductivity of the filtrate reached 100 μS/cm or less. Next, the thus separated filter cake was added and mixed with an aqueous solution containing 0.2 g of potassium nitrate at room temperature, and then dried at 120° C. under normal pressure over a whole day and night. The obtained dried powder was heated to 500° C. for 2 h while flowing air therethrough at a rate of 2.5 Nm$^3$/h, and then baked at the same temperature for 4 h, thereby obtaining about 20 g of a nickel/copper-based catalyst (A) composed of 35% by mass of nickel, 6% by mass of copper, 27% by mass of zirconium and 0.08% by mass of potassium.

PREPARATION EXAMPLE 2

Using 38.9 g of nickel nitrate hexahydrate, 10.9 g of copper nitrate hexahydrate, 31.6 g of an aqueous solution containing zirconium acetate in an amount of 15% by mass in terms of Zr, and 0.06 g of ammonium heptamolybdate tetrahydrate, the procedure for producing the catalyst A as described in the paragraph [0044] of JP 8-176074A was carried out, thereby obtaining about 20 g of a nickel/copper-based catalyst (B) composed of 33% by mass of nickel, 13% by mass of copper, 20% by mass of zirconium and 0.1% by mass of molybdenum.

EXAMPLE 1

A 500 mL autoclave of an electromagnetic induction rotary agitation type was charged with 150 g (0.55 mol) of stearyl alcohol and 2.0% by mass (on the basis of the raw alcohol) of the nickel/copper-based catalyst (A) produced in Preparation Example 1, and the contents of the autoclave were heated to 200° C. under normal pressure under stirring while flowing hydrogen therethrough at a rate of 1 L/h, and then subjected to catalytic reduction treatment for about 2 h. Thereafter, the obtained reaction mixture was cooled to 60° C. and taken out of the autoclave. The reaction mixture was charged again into a 500 mL autoclave of an electromagnetic induction rotary agitation type, and 47 g (2.76 mol) of ammonia was charged into the autoclave and further 0.17 mol of hydrogen was charged under pressure thereinto such that a whole pressure in the autoclave as measured at room temperature reached 2.3 MPaG. Next, the contents of the autoclave were heated to 220° C. as a reaction temperature while stirring (at 1000 rpm). The initial maximum pressure in the autoclave at 220° C. was 16 MPaG. While continuously supplying hydrogen into the autoclave such that a whole pressure therein was maintained at a constant pressure of 16 MPaG, the contents of the autoclave were reacted with each other for 5 h.

The resultant reaction product was filtered to remove the catalyst therefrom, and then subjected to gas chromatography to analyze a composition thereof. As a result, it was confirmed that the conversion of the raw alcohol (amount of alcohol consumed during reaction/amount of initial raw alcohol) was 98.6%; the selectivity to stearyl amine (amount of stearyl amine as a reaction product/amount of alcohol consumed during reaction) was 86.1%; the amount of distearyl amine produced was 12.6%; and the amount of the other by-products was 1.1%.

COMPARATIVE EXAMPLE 1

The same procedure as in Example 1 was repeated except for using the catalyst (B) produced in Preparation_Example 2 in place of the catalyst (A) and conducting the reaction for 6 h. The resultant reaction product was analyzed in the same manner as in Example 1. As a result, it was confirmed that the conversion of the raw alcohol was 98.0%; the selectivity to stearyl amine was 81.9%; the amount of distearyl amine produced was 14.4%; and the amount of the other by-products was 3.3%.

What is claimed is:

1. A process for producing an aliphatic amine, comprising the step of contacting a linear or branched, or cyclic aliphatic alcohol with ammonia and hydrogen in the presence of a catalyst consisting essentially of (A) nickel, copper and zirconium components, and (B) at least one metal component selected from the group consisting of elements belonging to Group 1 of the Periodic Table.

2. The process according to claim 1, wherein the aliphatic alcohol is an aliphatic alcohol having 6 to 22 carbon atoms.

3. The process according to claim 1, wherein the (B) at least one metal component selected from the group consisting of elements belonging to Group 1 of the Periodic Table in the catalyst is a potassium component.

4. The process according to claim 1, wherein a content of the (B) at least one metal component selected from the group consisting of elements belonging to Group 1 of the Periodic Table in the catalyst is from 0.02 to 10% by mass in terms of the metal element on the basis of a total amount of the catalyst.

5. The process according to claim 1, wherein the catalytic reaction of the aliphatic alcohol with ammonia and hydrogen is carried out at a temperature of from 120 to 280° C.

6. The process according to claim 1, wherein the catalytic reaction of the aliphatic alcohol with ammonia and hydrogen is carried out under such a condition that a molar ratio of ammonia to the aliphatic alcohol (ammonia/aliphatic alcohol) is from 0.5 to 10.

7. The process according to claim 1, wherein the catalyst is previously subjected to reducing treatment.

8. The process according to claim 1, wherein the catalyst is used in an amount of 0.1 to 20% by mass on the basis of the aliphatic alcohol.

9. The process according to claim 1, wherein the aliphatic amine is an aliphatic primary amine.

10. A catalyst capable of use in a process for producing an aliphatic amine by contacting a linear or branched, or cyclic aliphatic alcohol with ammonia and hydrogen, consisting essentially of (A) nickel, copper and zirconium components, and (B) at least one metal component selected from the group consisting of elements belonging to Group 1 of the Periodic Table.

11. The process according to claim 1, wherein (A) comprises, based on the amount of the catalyst, nickel in an amount of 10 to 55% by mass by mass in terms of metallic nickel; copper in an amount of 0.5 to 32% by mass in terms of metallic copper; and zirconium in an amount of 10 to 63% by mass in terms of metallic zirconium.

12. The process according to claim 1, wherein (A) comprises, based on the amount of the catalyst, nickel in an amount of 15 to 55% by mass in terms of metallic nickel; copper in an amount of 2 to 28% by mass in terms of metallic copper; and zirconium in an amount of 11 to 52% by mass in terms of metallic zirconium.

13. The process according to claim 1, wherein (A) comprises, based on the amount of the catalyst, nickel in an amount of 23 to 47% by mass in terms of metallic nickel; copper in an amount of 4 to 24% by mass in terms of metallic copper; and zirconium in an amount of 14 to 44% by mass in terms of metallic zirconium.

14. The process according to claim 4, wherein (B) comprises, based on the amount of the catalyst, from 0.03 to 2% by mass in terms of the metal element.

15. The process according to claim 4, wherein (B) comprises, based on the amount of the catalyst, from 0.05 to 1% by mass in terms of the metal element.

16. The process according to claim 5, wherein the temperature is from 180 to 250° C.

17. The process according to claim 6, wherein the molar ratio is from 2 to 7.

18. The process according to claim 8, wherein the amount is 0.5 to 10% by mass on the basis of the aliphatic alcohol.

* * * * *